United States Patent [19]  [11] 4,215,126
Durant et al. [45] Jul. 29, 1980

[54] ALKOXY PYRIDINE COMPOUNDS

[75] Inventors: Graham J. Durant; Charon R. Ganellin, both of Welwyn Garden City; George S. Sach, Welwyn, all of England

[73] Assignee: Smith Kline & French Laboratories Limited, Welwyn Garden City, Great Britain

[21] Appl. No.: 13,579

[22] Filed: Feb. 21, 1979

Related U.S. Application Data

[62] Division of Ser. No. 869,075, Jan. 13, 1978, Pat. No. 4,154,838, which is a division of Ser. No. 704,877, Jul. 13, 1976, Pat. No. 4,083,983.

[30] Foreign Application Priority Data

Jul. 31, 1975 [GB] United Kingdom ............... 31970/75

[51] Int. Cl.² .................... C07D 213/63; A61K 31/44

[52] U.S. Cl. ..................................... 424/263; 546/115; 546/296; 546/297; 546/300; 424/256

[58] Field of Search ............... 546/115, 296, 297, 300; 424/263, 256

[56] References Cited

U.S. PATENT DOCUMENTS

| | | | |
|---|---|---|---|
| 3,953,460 | 4/1976 | Durant et al. | 546/261 |
| 4,002,759 | 1/1977 | Durant et al. | 546/300 |

*Primary Examiner*—Alan L. Rotman
*Assistant Examiner*—Natalia Harkaway
*Attorney, Agent, or Firm*—Joan S. Keps; Richard D. Foggio; William H. Edgerton

[57] ABSTRACT

The compounds are alkoxypyridine compounds which are histamine H₂-antagonists. Two specific compounds of the present invention are N-cyano-N'-methyl-N''-[2-((3-methoxy-2-pyridyl)methylthio)ethyl]guanidine and 1-methylamino-1-[2-((3-methoxy-2-pyridyl)methylthio)ethylamino]-2-nitroethylene.

16 Claims, No Drawings

ALKOXY PYRIDINE COMPOUNDS

This is a division of application Ser. No. 869,075 filed Jan 13, 1978 now U.S. Pat. No. 4,154,838 which is a division of application Ser. No. 704,877 filed July 13, 1976, now U.S. Pat. No. 4,083,983.

This invention relates to pharmacologically active compounds, to pharmaceutical compositions containing these compounds and to methods of blocking histamine $H_2$-receptors by administering these compounds. The compounds of the invention can exist as acid addition salts but, for convenience, reference will be made throughout this specification to the parent compounds.

Many physiologically active substances elicit their biological actions by interaction with specific sites known as receptors. Histamine is such a substance and has a number of biological actions. Those biological actions of histamine which are inhibited by drugs commonly called "antihistamines", of which mepyramine, diphenhydramine and chlorpheniramine are typical examples, are mediated through histamine $H_1$-receptors (Ash and Schild, Brit. J. Pharmac. Chemother, 27, 427, (1966)). However, other of the biological actions of histamine are not inhibited by "antihistamines" and actions of this type which are inhibited by a compound described by Black et al. (Nature, 236, 385 (1972)) and called burimamide are mediated through receptors which are defined by Black et al. as histamine $H_2$-receptors. Thus histamine $H_2$-receptors may be defined as those histamine receptors which are not blocked by mepyramine but are blocked by burimamide. Compounds which block histamine $H_2$-receptors are referred to as histamine $H_2$-antagonists.

Blockade of histamine $H_2$-receptors is of utility in inhibiting the biological actions of histamine which are not inhibited b "antihistamines". Histamine $H_2$-antagonists are therefore useful, for example, as inhibitors of gastric acid secretion, as anti-inflammatory agents and as agents which act on the cardiovascular system, for example as inhibitors of the effects of histamine on blood pressure. In the treatment of certain conditions, for example inflammation and in inhibiting the actions of histamine on blood pressure, a combination of histamine $H_1$- and $H_2$-antagonists is useful.

The compounds of this invention are histamine $H_2$-antagonists.

The compounds of this invention are represented by Formula 1:

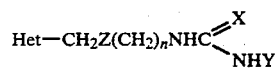

FORMULA I where Het is a grouping of the formula:

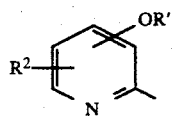

wherein R' is lower alkyl or $-(CH_2)_pA$ where p is 2 to 4 and A is hydroxy, lower alkoxy or dimethylamino; $R^2$ is hydrogen, lower alkyl, lower alkoxy, amino, halogen, or methylamino; or $-OR'$ and $R^2$ can together form a $-O(CH_2)_qO-$ group attached to adjacent carbon atoms on the pyridine ring, where q is 1 to 4; Z is sulphur or methylene; n is 2 or 3; X is sulphur, $CHNO_2$, NH, NCN or NOH; Y is hydrogen, lower alkyl, 2-hydroxyethyl or Het'$CH_2Z'(CH_2)_{n'}-$, where Het' has the same scope as Het in Formula 1 or is an imidazolyl ring optionally substituted by methyl or bromo, a pyridyl ring optionally substituted by hydroxy, chlorine or bromine, a thiazolyl ring or an isothiazolyl ring; Z' is sulphur, or methylene; and n' is 2 or 3 or a pharmaceutically acceptable acid addition salt thereof.

Throughout the present specification by the term "lower alkyl" we mean an alkyl group containing from 1 to 4 carbon atoms, and by the term "lower alkoxy" we mean an alkoxy group containing from 1 to 4 carbon atoms. It will be understood that the structure illustrated in Formula 1 is only one of several possible representations and that other tautomeric forms are also covered by the present invention. Hydrates, pharmaceutically acceptable salts and hydrated pharmaceutically acceptable salts of compounds of Formula 1 are also covered by the present invention.

It is preferred that the 6-position of the pyridine ring or rings in the compounds of Formula 1 is unsubstituted.

It is further preferred that $-OR'$ and $R^2$ are in the 3 and 4 positions of the pyridine ring comprising Het, and when $R^2$ is hydrogen it is preferred that $-OH'$ is in the 3 position of the pyridine ring comprising Het.

It is found that a particularly useful series of compounds are those wherein R' is lower alkyl, particularly methyl.

It is also preferred that Z is sulphur. Also preferably n is 2.

Particularly useful compounds according to our invention are those wherein X is $CHNO_2$ or NCN. A further preferance is that Y should be lower alkyl, particularly methyl, or Het'$CH_2Z'(CH_2)_{n'}-$ where Het+, Z' and n' are identical to Het, Z and n.

Specific compounds within the scope of the present invention include:
1-methylamino-1-[2-(3-methoxy-2-pyridylmethylthio)ethylamino]-2-nitroethylene,
1-methylamino-1-[2-(3-ethoxy-2-pyridylmethylthio)ethylamino]-2-nitroethylene,
1-methylamino-1-[2-(4-methoxy-2-pyridylmethylthio)ethylamino]-2-nitroethylene,
N-cyano-N'-methyl-N"-[2-(3-methoxy-2-pyridylmethylthio)ethyl]-guanidine,
N-cyano-N'-methyl-N"-[2-(3-ethoxy-2-pyridylmethylthio)ethyl]-guanidine,
N-cyano-N'-methyl-N"-[2-(4-methoxy-2-pyridylmethylthio)ethyl]-guanidine,
N-cyano-N'-methyl-N"-[2-(3,4-dimethoxy-2-pyridylmethylthio)ethyl]guanidine,
N-cyano-N'-methyl-N"-[2-(3-chloro-4-methoxy-2-pyridylmethyl-thio)ethyl]guanidine,
N-cyano-N'-methyl-N"-[4-(3-methoxy-2-pyridyl)-butyl]guanidine.

The compounds of Formula 1 wherein X is $CHNO_2$, NH or NCN may be prepared by a process which comprises the step:-

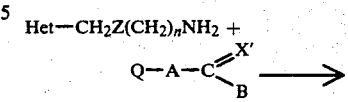

Formula 2
Formula 3

-continued

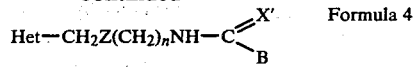

Formula 4

In Formulas 2, 3 and 4 Het, Z and n are as defined in Formula 1, Q is lower alkyl; A is sulphur, oxygen, or when X' is CHNO$_2$ and B is SQ', SO; X' is CHNO$_2$, NCOC$_6$H$_5$ or NCN; and B is SQ', OQ', where Q' is lower alkyl, or NHY where Y is as defined in Formula 1.

Compounds of Formula 4 wherein B is lower alkoxy or (lower alkyl)thio and X' is CHNO$_2$ or NCN may be converted into the corresponding compounds of Formula 1 by treatment with an amine NH$_2$Y, wherein Y is as defined in Formula 1.

Compounds of Formula 4 wherein X' is NCOC$_6$H$_5$ or NCN and B has the same scope as NHY in Formula 1 may be converted into the corresponding compounds of Formula 1 wherein X is NH by acid hydrolysis.

Compounds of Formula 4 wherein X' is NCOC$_6$H$_5$ or NCN and B is lower alkoxy or (lower alkyl)thio may be converted into compounds of Formula 1 wherein X is NH by treatment with an amine NH$_2$Y, where Y is as defined in Formula 1, and acid hydrolysis of the product.

Some preferred processes which fall within this general scheme are:-

(1) When QA and B are both methylthio and X' is NCN in Formula 3. Dimethyl N-cyanodithioimidocarbonate is treated with a solution of one equivalent of an amine of Formula 2 at about room temperature, and the resultant N-cyanoisothiourea is treated with an excess of an amine NH$_2$Y, where Y is as defined in Formula 1.

When X is NCN it is generally preferred that QA is methylthio, and B is methylthio or NHY.

(2) When QA is methylsulphinyl, B is methylthio and X' is CHNO$_2$ in Formula 3. 1-Methylthio-1-methylsulphinyl-2-nitroethylene is treated with a solution of one equivalent of an amine of Formula 2 at about room temperature, and the resultant substituted 1-methylthio-2-nitroethylene is treated with an excess of an amine NH$_2$Y is as defined in Formula 1. When X is CHNO$_2$ it is generally preferred that QA is methylthio and B is methylsulphinyl or NHY.

(3) When QA and B are both methylthio and X' is CHNO$_2$ or NCN in Formula 3. N-Cyano dimethyldithioimidocarbonate or 1,1-bis-methylthio-2-nitroethylene is treated with at least two equivalents of an amine of Formula 2 and the mixture is heated in pyridine to give a compound of Formula 1 wherein X is CHNO$_2$ or NCN and Y is Het'CH$_2$Z'(CH$_2$)$_{n'}$— where Het', Z' and n' are identical to Het, Z and n.

(4) When QA and B are both methylthio and X' is NCOC$_6$H$_5$ in Formula 3. N-Benzoyl dimethyldithioimidocarbonate is treated with at least two equivalents of an amine of Formula 2 and the mixture is heated in pyridine and the product hydrolysed under acidic conditions to give a compound of Formula 1 wherein X is NH and Y is Het'CH$_2$Z'(CH$_2$)$_{n'}$— where Het', Z' and n' are identical to Het, Z and n.

The compounds of Formula 1 wherein X is sulphur may be prepared by treating a compound of the formula L-E, where L is benzoyl, lower alkyl, 2-hydroxyethyl or Het—CH$_2$Z(CH$_2$)$_n$— and E is NCS or NHCS.SMe, with an amine of formula MNH$_2$ where M is Het—CH$_2$Z(CH$_2$)$_n$— when L is benzoyl, lower alkyl or 2-hydroxyethyl, or M is Y when L is Het-CH$_2$Z(CH$_2$)$_n$—. Products where L is benzoyl are hydrolysed under acid conditions to give compounds of Formula 1 wherein Y is hydrogen. Symmetrical compounds of Formula 1 wherein X is sulphur and Y is Het'CH$_2$Z'(CH$_2$)$_n$— where Het', Z' and n' are identical to Het, Z and n in Formula 1 may be prepared by treating carbon disulphide with at least two equivalents of an amine of Formula 2. The compounds of Formula 1 wherein X is NOH may be prepared by S-alkylating thioureas of Formula 1 wherein X is sulphur, for example by treatment with an alkyl halide, and treating the resultant isothiourea with hydroxylamine.

The amines of Formula 2 wherein Z is sulphur may be prepared by treating a compound of Formula 5.

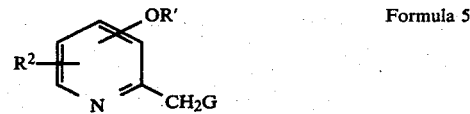

Formula 5 wherein G is chlorine, bromine or hydroxy, and R' and R$^2$ are as defined in Formula 1, with a mercaptoalkylamine of formula HS(CH$_2$)$_n$NH$_2$ where n is 2 or 3. When G is chlorine or bromine the reaction is carried out under basic or substantially neutral conditions, and when G is hydroxy the reaction may be carried out under acidic conditions which do not affect the alkoxy substituent.

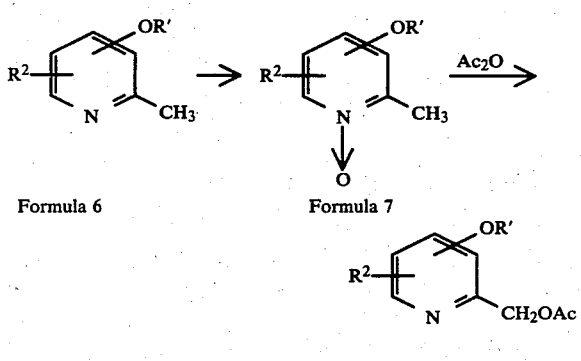

Formula 6    Formula 7

Formula 8

Compounds of Formula 6 may be prepared by standard methods of pyridine chemistry and, for example, R' may be introduced by O-alkylation of the corresponding hydroxypyridine or by alkoxide displacement on a 4- or 6-halo picoline. Compounds of Formula 6 where OR' and R$^2$ form a —O(CH$_2$)$_q$O— group may be prepared by alkylating the corresponding dihydroxypyridine compound under basic conditions with Hal—(CH$_2$)$_q$Hal, where Hal is chlorine or bromine.

The compounds of Formula 6 may be converted into the corresponding N-oxides of Formula 7 by treatment with a peroxybenzoic acid, such as m-chloroperoxybenzoic acid, and these N-oxides may be rearranged into the corresponding 2-(acetoxymethyl)pyridines of Formula 8 by heating in acetic anhydride. These acetoxy derivatives may be hydrolyzed under acidic conditions to give 2-(hydroxymethyl)pyridines, which may be converted into the corresponding 2-(chloromethyl)-pyridines e.g., by treatment with thionyl chloride.

An alternative method of preparation of 2-(bromomethyl)-pyridines of Formula 5 wherein G is bromine, and R$^2$ is other than lower alkyl is the direct bromination of a picoline of Formula 6 under controlled conditions e.g., with N-bromosuccinimide.

The compounds of Formula I block histamine $H_2$-receptors, that is they inhibit the biological actions of histamine which are not inhibited by "antihistamines" such as mepyramine but are inhibited by burimamide. For example, the compounds of this invention have been found to inhibit histamine-stimulated secretion of gastric acid from the lumen-perfused stomachs of rats anaesthetized with urethane, at doses of from 0.5 to 256 micromoles per kilogram intravenously. This procedure is referred to in the above mentioned paper of Ash and Schild. The activity of these compounds as histamine $H_2$-antagonists is also demonstrated by their ability to inhibit other actions of histamine which, according to the above mentioned paper of Ash and Schild, are not mediated by histamine $H_1$-receptors. For example, they inhibit the actions of histamine on the isolated guinea pig atrium and isolated rat uterus.

The compounds of this invention inhibit the basal secretion of gastric acid and also that stimulated by pentagastrin or by food.

In addition, the compounds of this invention show antiinflammatory activity. In conventional tests such as the rat paw oedoma test, where the oedema is induced by an irritant, the rat paw volume is reduced by subcutaneous injection of doses of about 500 micromoles/Kg of a compound of Formula 1. In a conventional test, such as the measurement of blood pressure in the anaesthetized rat, the action of the compounds of this invention in inhibiting the vasodilator action of histamine can also be demonstrated. The level of activity of the compounds of this invention is illustrated by the effective dose producing 50% inhibition of gastric acid secretion in the anaesthetized rat and the dose producing 50% inhibition of histamine-induced tachycardia in the isolated guinea pig atrium.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric and maleic acids and may conveniently be formed from the corresponding bases of Formula I by standard procedures, for example by treating the base with an acid in a lower alkanol or by the use of ion exchange resins to form the required salt either directly from the base or from a different addition salt.

Pharmaceutical compositions comprising a pharmaceutical carrier and a compound of Formula I or a pharmaceutically acceptable acid addition salt thereof and methods of blocking histamine $H_2$-receptors which comprise administering to an animal a compound of Formula I or a pharmaceutically acceptable acid addition salt thereof are also objects of this invention. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 g. If a liquid carrier is used, the preparation may be in the form of a syrup, emulsion, soft gelatin capsule, sterile injectable liquid contained for example in an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the compositions in an effective amount to block histamine $H_2$-receptors. The route of administration may be oral or parenteral.

Preferably, each dosage unit will contain the active ingredient in an amount of from about 50 mg to about 250 mg.

The active ingredient will preferably be administered one to six times per day. The daily dosage regimen will preferably be from about 150 mg to about 1500 mg.

Advantageously the composition will be made up in a dosage form appropriate to the desired mode of administration, for example as a tablet, capsule, injectable solution or as a cream or ointment for topical application.

The invention is illustrated but in no way limited by the following Examples in which all temperatures are in degrees Centigrade:-

EXAMPLE 1

N-cyano-N'-methyl-N''-[2-(3-methoxy-2-pyridylmethylthio)-ethyl]guanidine.

(i) (a) 3-Hydroxy-2-hydroxymethylpyridine (4.4 g) was added to a solution of sodium (0.81 g) in methanol (50 ml). The solvent was evaporated off and the residue was treated with toluene, evaporated and the residue taken up in dimethylsulphoxide (88 ml). Methyliodide (5.0 g) in dimethylsulphoxide (12 ml) was added while the solution was stirred for 30 minutes at 18°. After standing overnight the solvent was removed and the residue was partitioned between chloroform and water. The chloroform extract was evaporated and a solution of the residue in ethanol was treated with ethanolic hydrogen chloride to yield 2-hydroxymethyl-3-methoxypyridine hydrochloride (3.0 g), m.p. 208° dec.

(b) 3-Hydroxypyridine-2-carboxylic acid (50 g) was refluxed for 6 hours with a methanolic solution of boron trifluoride. After cooling, treatment with sodium bicarbonate solution, extraction with ether and evaporation of the solvent crude 3-hydroxy-2-methoxycarbonylpyridine was obtained which was recrystallised from ether to give the pure ester (27.4 g), m.p. 75°–76.5°.

Treatment of 3-hydroxy-2-methoxycarbonylpyridine (7.6 g) with sodium (1.2 g) in methanol (20 ml) gave a clear solution which was evaporated and the residue was dissolved in dimethylsulphoxide (120 ml) and treated with a solution of methyl iodide (7.3 g) in dimethylsulphoxide (30 ml). After standing at room temperature for 60 hours the solvent was removed and the residue was dissolved in water and extracted with dichloromethane. The dichloromethane extract was evaporated and the residue was converted into the hydrochloride salt with ethanolic hydrogen chloride to yield 3-methoxy-2-methoxycarbonylpyridine hydrochloride (7.7 g), m.p. 162°–163.5° (dec).

Sodium borohydride (6.3 g) was added slowly over 75 minutes to a solution of 3-methoxy-2-methoxycarbonylpyridine (9.2 g) in ethanol. Methanol (100 ml) was then added and after the initial vigorous reaction had subsided, further sodium borohydride (8.3 g) was added over a further 3 hours, and the mixture was left to stand overnight. The solvent was evaporated, the residue dissolved in water and extracted with chloroform and the chloroform solution dried. Evaporation, and crystallisation from ether gave 2-hydroxymethyl-3-methoxypyridine (4.4 g) m.p. 72.5°–73.5°.

(ii) 2-Hydroxymethyl-3-methoxypyridine (4.2 g) was dissolved in chloroform (60 ml) and to the stirred solution was added thionyl chloride (6 ml). The mixture was stirred for 90 minutes and the solvent evaporated and the residue was recrystallised from ethanol/ether to give 2-chloromethyl-2-methoxypyridine hydrochloride (5.1 g), m.p. 171.5°–172.5°.

(iii) To a solution of sodium (1.65 g) in ethanol (75 ml) was added cysteamine hydrochloride (2.9 g) and after stirring for 5 minutes a solution of 2-chloromethyl-3-methoxypyridine hydrochloride (4.5 g) in ethanol (75 ml) was added over 25 minutes. The mixture was stirred for 2 hours at 15° and the sodium chloride was filtered off and the filtrate was evaporated to give 2-[2-aminoethylthiomethyl]-3-methoxypyridine (4.6 g) as a colourless oil.

(iv) A solution of 2-[2-aminoethylthiomethyl]-3-methoxypyridine (2.1 g) in ethanol (15 ml) was added over one hour to a stirred solution of dimethyl N-cyanodithioimidocarbonate (1.5 g) in ethanol (15 ml). The mixture was allowed to stand overnight and nitrogen was bubbled through for one hour. The crystalline precipitate was recrystallised from ethanol/ether to yield N-cyano-N'-[2-((3-methoxy-2-pyridyl)methylthio)ethyl]-S-methylisothiourea (2.2 g), m.p. 102°–103°.

(Found: C, 48.4; H, 5.4; N, 19.0% $C_{12}H_{16}N_4OS_2$ requires: C, 48.6; H, 5.4; N, 18.9%.)

(v) N-cyano-N'-[2-((3-methoxy-2-pyridyl)methylthio)ethyl]-S-methylisothiourea (1.9 g) in ethanol (10 ml) was treated with ethanolic methylamine (20 ml 33% solution) and the resultant clear solution was allowed to stand overnight. Excess of methylamine was removed by bubbling nitrogen through the solution and the crystalline precipitate was recrystallised from ethanol to yield the title product (1.2 g), m.p. 122°–123°.

(Found: C, 51.4; H, 6.1; N, 25.0; S, 11.4; $C_{12}H_{17}N_5OS$ requires: C, 51.6; N, 6.1; N, 25.1; S, 11.5%)

EXAMPLE 2

1-Methylamino-1-[2-((3-methoxy-2-pyridyl)methylthio)ethylamino]-2-nitroethylene (i) A solution of 2-[2-aminoethylthiomethyl]-3-methoxy-1-pyridine (2.1 g) in methanol (33 ml) was added over 25 minutes to a stirred solution of 1-methylthio-1-methylsulphinyl-2-nitroethylene (2.1 g) in methanol (75 ml) at 30°. After standing for an hour the solution was concentrated to give a yellow-brown oil which was crystallised from ethanol/ether to yield 1-methylthio-1-[2-((3-methoxy-2-pyridyl)methylthio)ethylamino]-2-nitroethylene (1.9 g), m.p. 87.5°–88.5°.

(Found: C, 45.5; H, 5.4; N, 13.3; $C_{12}H_{17}N_3O_3S_2$ requires: C, 45.7; H, 5.4; N, 13.3%)

(ii) 1-Methylthio-1-[2-((3-methoxy-2-pyridyl)methylthio)ethylamino]-2-nitroethylene (1.4 g) was stirred with a solution of methylamine in ethanol (25 ml, 33% solution) and dissolved within a minute. After a further 3 minutes a crystalline product separated and recrystallisation from ethanol/ether yielded the title product (1.1 g), m.p. 145.5°–147°.

(Found: C, 48.1; H, 6.1; N, 18.7; S, 10.8; $C_{12}H_{18}N_4O_3S$ requires: C, 48.3; H, 6.1; N, 18.8; S, 10.8%.

EXAMPLE 3

N-Cyano-N'-methyl-N''-[2-((3-ethoxy-2-pyridyl)methylthio)ethyl]guanidine.

(i) 3-Hydroxy-2-hydroxymethylpyridine (8.5 g) was added to a solution of sodium (1.565 g) in ethanol (100 cc) and the mixture was evaporated to dryness. Dimethylsulphoxide (180 cc) was added to the residue, and bromoethane (7.43 g) in dimethylsulphoxide (24 cc) was added over 20 minutes to the stirred mixture. The mixture was allowed to stand at room temperature for 65 hours, and was evaporated. The residue was partitioned between chloroform and water, and the chloroform extracts were evaporated to an oil which was converted into a crystalline hydrochloride m.p. 190°–191.5° by the addition of ethanolic hydrogen chloride. The hydrochloride was dissolved in water, and aqueous ammonia was added until the mixture was basic, and the mixture was extracted with chloroform. The chloroform extracts were evaporated and the residue crystallised from ethanol/diethyl ether to give 3-ethoxy-2-hydroxymethylpyridine (5.0 g) m.p. 74.5°–76°.

(ii) Thionyl chloride (8 cc) was added over 8 minutes to a stirred solution of 3-ethoxy-2-hydroxymethylpyridine (5.6 g) in chloroform (60 cc) at room temperature. After 1½ hrs t mixture was evaporated to dryness and the residue was recrystallised from 0.16 M ethanolic hydrogen chloride/diethyl ether (1:1) to give 2-chloromethyl-3-ethoxypyridine hydrochloride (6.5 g) m.p. 176°–179.5°. (decomp.).

(iii) Cysteamine hydrochloride (2.76 g) was added to a stirred mixture of sodium (1.576 g) in ethanol (75 cc) at 12°, 2-Chloromethyl-3-ethoxypyridine hydrochloride (4.60 g) in ethanol (70 cc) was added over 30 minutes to this mixture stirred at 10°–12°. The mixture was left to stand overnight, filtered and the filtrate was evaporated to dryness. The residue was dissolved in water, acidified to pH 4 with hydrochloric acid and extracted with chloroform (discarded). The aqueous phase was adjusted to pH 12 with aqueous sodium hydroxide and was extracted with chloroform. The chloroform extracts were evaporated to give 2-(2-aminoethylthiomethyl)-3-ethoxypyridine (4.2 g) as an oil.

(iv) 2-(2-Aminoethylthiomethyl)-3-ethoxypyridine (1.0 g) in ethanol (10 cc) was added over 45 minutes to a stirred solution of dimethyl N-cyanodithioimidocarbonate (0.690 g) in ethanol (5 cc) at room temperature. The mixture was allowed to stand overnight at room temperature, nitrogen was bubbled through the solution for one hour, and the mixture was allowed to crystallise to give N-cyano-N'-[2-((3-ethoxy-2-pyridyl)methylthio)ethyl]-S-methylisothiourea (1.4 g) m.p. 98°–99°.

(v) Methylamine in ethanol (33%, 10 cc) was added to a stirred suspension of N-cyano-N'-[2-((3-ethoxy-2-pyridyl)-methylthio)ethyl]-S-methylisothiourea (1.0 g) in ethanol (5 cc) and the mixture was left to stand overnight. Nitrogen was bubbled through the solution for one hour and the solution was concentrated and crystals which deposited were filtered off and recrystallised from ethanol/ether to give the title product (0.7 g) m.p. 126.5°–127.5°.

(Found: C, 53.4; H, 6.7; N, 23.9; S, 10.7; $C_{13}H_{19}N_5OS$ requires: C, 53.2; H, 6.5; H, 23.9; S, 10.9%).

EXAMPLE 4

1-Methylamino-2-(3-ethoxy-2-pyridylmethylthio)ethylamino]-2-nitroethylene (i) 2-(2-Aminoethylthiomethyl)-3-ethoxypyridine (2.2 g) in methanol (35 cc) was added over 25 minutes to a stirred solution of 1-methylthio-1-methylsulphinyl-2-nitroethylene (2.07 g) in methanol (85 ml) at 27°–30°, and the mixture was left overnight at room temperature. The mixture was evaporated to a residual oil which was triturated with ethanol/ether to give 1-methylthio-1-[2-(3-ethoxy-2-pyridylmethylthio)ethylamino]-2-nitroethylene (1.68 g) m.p. 126°–127°.

(ii) Methylamine in ethanol (33%, 25 cc) was added to 1-methylthio-1-[2-(3-ethoxy-2-pyridylmethylthio)ethylamino]-2-nitro ethylene (1.32 g) and the mixture was stirred at 40° for 1 hour and 1 hour at room temperature. Nitrogen was bubbled through the mixture for 1 hour and the precipitate was recrystallised from ethanol/ether to give the title product (0.52 g) m.p. 130°–131°.

(Found: C, 50.2; H, 6.6; N, 18.0; S, 10.3; $C_{13}H_{20}N_4O_3S$ requires: C, 50.0; H, 6.5; N, 17.9; S, 10.3%)

EXAMPLE 5

N-Cyano-N'-methyl-N''-[2-((4-methoxy-2-pyridyl)methylthio)ethyl]guanidine.

(1) Thionyl chloride (23 cc) was added over 25 minutes to a stirred solution of 2-hydroxymethyl-4-methoxypyridine (8.935 g) in chloroform at room temperature, and the mixture was stirred for a further 2 hours and was evaporated to dryness and the residue was triturated with ether and recrystallised from 0.9 N ethanolic hydrogen chloride/ether (7:5) to give 2-chloromethyl-4-methoxypyridine hydrochloride m.p. 142° (decomp).(12.1 g).

(ii) Cysteamine hydrochloride (7.62 g) was added to a solution of sodium (4.70 g) in ethanol (170 cc) and the mixture was stirred and cooled to 10° and 2-chloromethyl-4-methoxypyridine hydrochloride (11.5 g) in methanol (50 cc) was added over 35 minutes, and the mixture was left overnight at room temperature. The mixture was filtered and the filtrate was evaporated to a residue which was partitioned between chloroform and water. The chloroform extract was evaporated to an oil which was crystallised from 2.1 M ethanolic hydrogen chloride to give 2-(2-aminoethylthiomethyl)-4-methoxypyridine dihydrochloride (12.4 g) m.p. 172.5° (decomp).

(iii) A solution of 2-(2-aminoethylthiomethyl)-4-methoxypyridine (3.15 g) in ethanol (25 cc) was added over 1 hour to a stirred solution of dimethyl N-cyanodithioimidocarbonate (2.215 g) in ethanol (30 cc) at 22° and the mixture was allowed to stand overnight at room temperature. Nitrogen was passed through the suspension and the mixture was filtered to give N-cyano-N'-[2-((4-methoxy-2-pyridyl)methylthio)ethyl]-S-methylisothiourea m.p. 91.5°–92.5°. (3.9 g).

(iv) Methylamine in ethanol (33%, 20 cc) was added to a stirred solution of N-cyano-N'-[2-((4-methoxy-2-pyridyl)methylthio)ethyl]-S-methylisothiourea (3.56 g) in ethanol (25 cc) at 35°, and the mixture was left to stand overnight. Nitrogen was bubbled through the solution and the crystals were filtered off to give the title product, (2.74 g) m.p. 121°–122°.

Found: C, 51.8; H, 6.2; N, 25.0; S, 11.4; $C_{12}H_{17}N_5OS$ requires: C, 51.6; H, 6.1; N, 25.1; S, 11.5%).

EXAMPLE 6

1-Methylamino-1-[2-(4-methoxy-2-pyridylmethylthio)ethylamino]-2-nitroethylene (i) A solution of 2-(2-aminoethylthiomethyl)-4-methoxypyridine (3.28 g) in methanol (40 cc) was added over 70 minutes to a stirred solution of 1-methylthio-1-methylsulphinyl-2-nitroethylene (3.01 g) in methanol (200 cc) at 30°. The mixture was allowed to stand overnight at room temperature and was evaporated to an oil which was crystallised from aqueous ethanol to give 1-methylthio-1-[2-(4-methoxy-2-pyridylmethylthio)ethylamino)-2-nitroethylene monohydrate (3.04 g) m.p. 52.5°–54.5°.

(ii) Methylamine in ethanol (33%, 20 cc) was added to 1-methylthio-1-[2-(4-methoxy-2-pyridylmethylthio)ethylamino]2-nitroethylene monohydrate (2.01 g) and the mixture was stirred at 18° for 20 minutes and evaporated to an oil which was crystallised from propan-2-ol to give the title product (1.1 g) m.p. 107°–108.5°.

Found: C, 48.2; H, 6.0; N, 18.5; S, 10.6; $C_{12}H_{18}N_4O_3S$ requires: C, 48.3; H, 18.8; S, 10.8%).

EXAMPLE 7

By reaction of 2-[2-aminoethylthiomethyl]-3-methoxypyridine with methyl isothiocyanate there may be produced N-methyl-N'-[2-((3-methoxy-2-pyridyl)methylthio)ethyl]thiourea.

EXAMPLE 8

Reaction of N-methyl-N'-[2-((3-methoxy-2-pyridyl)methylthio)ethyl]thiourea (from Example 7) with methanolic hydrogen chloride yields N,S-dimethyl-N'-[2-((3-methoxy-2-pyridyl)-methylthio)ethyl]isothiourea dihydrochloride which, when treated with hydroxylamine hydrochloride yielded N-hydroxy-N'-methyl-N''-[2-((3-methoxy-2-pyridyl)methylthio)ethyl]guanidine.

EXAMPLE 9

When S-methyl-N-cyano-N'-[2-((3-methoxy-2-pyridyl)methylthio)ethyl]isothiourea (from Example 1 (iv) is refluxed in pyridine for 6 hours with 2-[2-aminoethylthiomethyl]-3-methoxypyridine, the product which is obtained is N-cyano-N,N'-bis[2-((3-methoxy-2-pyridyl)methylthio)ethyl]guanidine.

EXAMPLE 10

(i) Reaction of 2-chloro-3-nitropyridine with 2-(2-cyanoethyl)malonic acid diethyl ester and sodium hydride in tetrahydrofuran yields 1-(3-nitro-2-pyridyl)-1,1-bis-(carbethoxy)butyronitrile m.p. 93.5°–94.5° which after alkaline hydrolysis and acidification gives 2-(3-cyanopropyl)-3-nitropyridine hydrochloride 142°–145.5°. Reduction with hydrogen and palladium on charcoal and treatment of the product with sodium nitrite and sulphuric acid with subsequent warming gives 2-(3-cyanopropyl)-3-hydroxypyridine. Methylation with methyl iodide and sodium ethoxide in dimethylsulphoxide and subsequent reduction with lithium aluminium hydride gives 2-(4-aminobutyl)-3-methoxypyridine.

(ii) Reaction of 2-(4-aminobutyl)-3-methoxypyridine with dimethyl N-cyanodithioimidocarbonate and treatment of the product with methylamine according to the general procedure of Example 1(iv)(v) gives N-cyano-N'-methyl-N''-[4-(3-methoxy-2-pyridyl)butyl]guanidine.

(iii) Reaction of 2-(4-aminobutyl)-3-methoxypyridine with 1-methylthio-1-methylsulphinyl-2-nitroethylene and treatment of the product with methylamine according to the general procedure of Example 2 gives 1-nitro-2-methylamino-2-[4-(3-methoxy-2-pyridyl)-butylamino]ethylene.

(iv) Reaction of 2-(4-aminobutyl)-3-methoxypyridine with methyl isothiocyanate gives N-[4-(3-methoxy-2-pyridyl)butyl]-N'-methylthiourea.

EXAMPLE 11

When S-methyl-N-cyano-N'-[2-((3-methoxy-2-pyridyl)-methylthio)ethyl]isothiourea is heated in pyridine with the following amines:
(a) 2-(4-Aminobutyl)-3-methoxypyridine
(b) 4-(2-Aminoethylthiomethyl)imidazole
(c) 4-(2-Aminoethylthiomethyl)-5-methylimidazole
(d) 4-(2-Aminoethylthiomethyl)-5-bromoimidazole
(e) 2-(2-Aminoethylthiomethyl)pyridine
(f) 2-(2-Aminoethylthiomethyl)-3-chloropyridine
(g) 2-(2-Aminoethylthiomethyl)-3-bromopyridine
(h) 2-(2-Aminoethylthiomethyl)thiazole
(i) 3-(2-Aminoethylthiomethyl)isothiazole the following compounds may be obtained:
(a) N-cyano-N'-[2-((3-methoxy-2-pyridyl)methylthio)ethyl]-N''-[4-(3-methoxy-2-pyridyl)butyl]guanidine
(b) N-cyano-N'-[2-((3-methoxy-2-pyridyl)methylthio)ethyl]-N''-[2-(4-imidazolylmethylthio)ethyl]guanidine
(c) N-cyano-N'-[2-((3-methoxy-2-pyridyl)methylthio)ethyl]-N''-[2-(5-methyl-4-imidazolylmethylthio)ethyl]guanidine
(d) N-cyano-N'-[2-((3-methoxy-2-pyridyl)methylthio)ethyl]-N''-[2-(5-bromo-4-imidazolylmethylthio)ethyl]guanidine
(e) N-cyano-N'-[2-((3-methoxy-2-pyridyl)methylthio)ethyl]-N''-[2-(2-pyridylmethylthio)ethyl]guanidine
(f) N-cyano-N'-[2-((3-methoxy-2-pyridyl)methylthio)ethyl]-N''-[2-((3-chloro-2-pyridyl)methylthio)ethyl]guanidine
(g) N-cyano-N'-[2-((3-methoxy-2-pyridyl)methylthio)ethyl]-N''-[2-((3-bromo-2-pyridyl)methylthio)ethyl]guanidine
(h) N-cyano-N'-[2-((3-methoxy-2-pyridyl)methylthio)ethyl]-N''-[2-(2-thiazolylmethylthio)ethyl]guanidine
(i) N-cyano-N'-[2-((3-methoxy-2-pyridyl)methylthio)ethyl]-N''-[2-(3-isothiazolylmethylthio)ethyl]guanidine When the amines listed above are heated at 140° for 2 hours with 1-methylthio-1-[2-((3-methoxy-2-pyridyl)methylthio)ethylamino]-2-nitroethylene and the cooled melt is recrystallised the following compounds are prepared
(a) 1-[2-((3-methoxy-2-pyridyl)methylthio)ethyl]-1-[4-(3-methoxy-2-pyridyl)butyl]-2-nitroethylene
(b) 1-[2-((3-methoxy-2-pyridyl)methylthio)ethyl]-1-[2-(4-imidazolylmethylthio)ethyl]-2-nitroethylene
(c) 1-[2-((3-methoxy-2-pyridyl)methylthio)ethyl]-1-[2-(5-methyl-4-imidazolylmethylthio)ethyl]-2-nitroethylene
(d) 1-[2-((3-methoxy-2-pyridyl)methylthio)ethyl]-1-[2-(5-bromo-4-imidazolylmethylthio)ethyl]-2-nitroethylene
(e) 1-[2-((3-methoxy-2-pyridyl)methylthio)ethyl]-1-[2-(2-pyridylmethylthio)ethyl]-2-nitroethylene
(f) 1-[-((3-methoxy-2-pyridyl)methylthio)ethyl]-1-[2-((3-chloro-2-pyridyl)methylthio)ethyl]-2-nitroethylene
(g) 1-[2-((3-methoxy-2-pyridyl)methylthio)ethyl]-1-[2-((3-bromo-2-pyridyl)methylthio)ethyl]-2-nitroethylene
(h) 1-[2-((3-methoxy-2-pyridyl)methylthio)ethyl]-1-[2-(2-thiazolylmethylthio)ethyl]-2-nitroethtylene
(i) 1-[2-((3-methoxy-2-pyridyl)methylthio)ethyl]-1-[2-(3-isothiazolylmethylthio)ethyl]-2-nitroethylene

EXAMPLE 12

When
(a) 1-bromobutane
(b) 2-methoxyethyl bromide
(c) 2-dimethylaminoethyl chloride
(d) 2-benzyloxyethyl bromide
(e) 2-benzyloxybutyl bromide
(f) 2-ethoxyethyl bromide are substituted for bromoethane in the procedure of Example 3(i) and the products are successively treated with thionyl chloride, cysteamine, dimethyl N-cyanodithioimidocarbonate and methylamine according to the general procedures of Example 3(ii)–(v) the following compounds are obtained:
(a) N-Cyano-N'-methyl-N''-[2-((3-butoxy-2-pyridyl)methylthio)ethyl]guanidine
(b) N-Cyano-N'-methyl-N''-[2-((3-(2-methoxyethoxy)-2-pyridyl)methylthio)ethyl]guanidine
(c) N-Cyano-N'-methyl-N''-[2-((3-(2-dimethylaminoethoxy)-2-pyridyl)methylthio)ethyl]guanidine
(d) N-Cyano-N'-methyl-N''-[2-((3-(2-benzyloxyethoxy)-2-pyridyl)methylthio)ethyl]guanidine
which may be hydrogenolysed using palladium on charcoal catalyst to give N-cyano-N'-methyl-N''-[2-((3-(2-hydroxyethoxy)-2-pyridyl)methylthio)ethyl]guanidine
(e) N-Cyano-N'-methyl-N''-[2-((3-(4-benzyloxybutoxy)2-pyridyl)methylthio)ethyl]guanidine
which may be hydrogenolysed using palladium on charcoal catalyst to give N-cyano-N'-methyl-N''-[2-((3-(4-hydroxybutoxy)-2-pyridyl)methylthio)ethyl]guanidine
(f) N-Cyano-N'-methyl-N''-[2-((3-(2-ethoxyethoxy)-2-pyridyl)methylthio)ethyl]guanidine.

EXAMPLE 13

Substitution of 3-mercaptopropylamine hydrochloride for cysteamine hydrochloride in the general procedure of Example 1(iii) and successive treatment of the product according to the general procedures of Example 1(iv) and (v) leads to the production of N-cyano-N'-methyl-N''-[3((3-methoxy-2-pyridyl)methylthio)-propyl]guanidine.

EXAMPLE 14.

Substitution of butylamine for methylamine in the general procedures of Examples 1(v) and 2(ii) leads to the production of N-cyano-N'-butyl-N''-[2-((3-methoxy-2-pyridyl)methylthio)ethyl]guanidine and 1-butylamino-1-[2-((3-methoxy-2-pyridyl)methylthio)ethylamino]-2-nitroethylene.

EXAMPLE 15

Substitution of 5-hydroxy-2-hydroxymethylpyridine for 3-hydroxy-2-hydroxymethylpyridine in the procedure of Example 1 leads to the preparation of N-cyano-N'-methyl-N''-[2-((5-methoxy-2-pyridyl)methylthio)ethyl]guanidine.

EXAMPLE 16

Successive treatment of 6-methyl-2-pyridone with a mixture of phosphoryl chloride and phosphorus pentachloride, and sodium methoxide gives 6-methoxy-2-methylpyridine which may be converted into 2-bromomethyl-6-methoxypyridine with N-bromosuccinimide. Substitution of 2-bromomethyl-6-methoxypyridine for 2-chloromethyl-3-methoxypyridine in the general procedure of Example 1(iii)-(v) leads to the preparation of N-cyano-N'-methyl-N''-[2-((6-methoxy-2-pyridyl)methylthio)ethyl]guanidine.

EXAMPLE 17

Treatment of 3-hydroxy-2,4-dimethylpyridine with sodium methoxide and methyliodide in dimethylsulphoxide gives 3-methoxy-2,4-dimethylpyridine, which may be converted into the corresponding N-oxide with m-chloroperoxylbenzoic acid. Rearrangement of this N-oxide in actic anhydride followed by purification and deacetylation gives 2-hydroxymethyl-3-methoxy-4-methylpyridine, which may be substituted for 2-hydroxy-3-methoxypyridiue in the procedure of Example 1(ii)-(v) to prepare N-cyano-N'-methyl-N''-[2-((3-methoxy-4-methyl-2-pyridyl)methylthio)ethyl]guanidine.

EXAMPLE 18

3-Chloro-2-methylpyridine N-oxide may be nitrated with a mixture of nitric and sulphuric acids, and the 4-nitropyridine produced successively treated with sodium methoxide, heated in acetic anhydride, purified and deacetylated to give 2-hydroxymethyl-3-chloro-4-methoxypyridine, which may be substituted for 2-hydroxy-3-methoxypyridine in the procedure of Example 1(ii)-(v) to prepare N-cyano-N'-methyl-N''-[2-((3-chloro-4-methoxy-2-pyridyl)-methylthio)ethyl]-guanidine.

EXAMPLE 19

(i) 3-Hydroxy-2-methylpyridine may be successively methylated with methyl iodide and sodium methoxide in dimethylsulphoxide, treated with m-chloroperoxybenzoic acid and nitrated with a mixture of nitric and sulphuric acid to give 4-nitro-3-methoxy-2-methylpyridine N-oxide.

(2) 4-Nitro-3-methoxy-2-methylpyridine N-oxide may be converted into 2-hydroxymethyl-3,4-dimethoxypyridine by reaction with sodium methoxide, rearrangement of the N-oxide in acetic anhydride, purification and deacetylation, and this hydroxymethyl derivative may be converted into N-cyano-N'-methyl-N''-[2-((3,4-dimethoxy-2-pyridyl)methylthio)ethyl]guanidine by the procedure of Example 1(ii)-(v).

EXAMPLE 20

(i) 4-Nitro-3-methoxy-2-methylpyridine N-oxide is heated in acetic anhydride and the purified product is deacetylated and reduced with hydrogen and palladium on charcoal to give 4-amino-2-hydroxymethyl-3-methoxypyridine.

(ii) 4-Amino-2-hydroxymethyl-3-methoxypyridine is diazotised in dilute sulphuric acid with sodium nitrite and the diazonium compound is warmed to give 4-hydroxy-2-hydroxymethyl-3-methoxypyridine which may be demethylated with hydrobromic acid (iii) Alkylation of 3,4-dihydroxy-2-hydroxymethylpyridine with pelleted sodium hydroxide and
  (a) Dibromomethane
  (b) 1,2-Dibromoethane
  (c) 1,4-Dibromobutane leads to the production of (a) 4-hydroxymethyl (1,3,-dioxole[4,5-c]pyridine) (b) 2,3-Dihydro-5-hydroxymethyl(p-dioxino[2,3-c]pyridine) (c) 2,3,4,5-Tetrahydro-7-hydroxymethyl-(1,4-dioxocino[2,3-c]pyridine) which may be converted into
  (a) N-cyano-N'-methyl-N''-[2-(4-(1,3-dioxolo[4,5-c]pyridyl)methylthio)ethyl]guanidine
  (b) N-cyano-N'-methyl-N''-[2-(5-(2,3-dihydro-p-dioxino[3,3-c]pyridyl)methylthio)ethyl]guanidine
  (c) N-cyano-N'-methyl-N''-[2-(7-(2,3,4,5-tetrahydro-1,4-dioxocino[2,3-c]pyridyl)methylthio)ethyl]guanidine
by the procedure of Example 1(ii)-(v).

EXAMPLE 21

(a) Selective N-acetylation of 4-amino-2-hydroxymethyl-3-methoxypyridine gives 4-acetylamino-2-hydroxymethyl-3-methoxypyridine.

(b) N-Trifluoracetylation of 4-amino-2-hydroxymethyl-3-methoxypyridine with trifluoracetic anhydride, N-methylation of the trifluoracetyl derivative, deprotection and selective N-acetylation of the product gives 4-(N-methyl-N-acetylamino)-2-hydroxymethyl-3-methoxypyridine.

(c) Substitution of
  (1) 4-acetylamino-2-hydroxymethyl-3-methoxypyridine
  (2) 4-(N-methyl-N-acetylamino)-2-hydroxymethyl-3-methoxypyridine,
in the general procedure of Example 1(ii) and (iii), deacetylation of the product under acidic conditions and treatment according to the general procedure of Example 1(iv) and (v) leads to the production of
  (1) N-cyano-N'-methyl-N''-[2-((4-amino-3-methoxy-2-pyridyl)methylthio)ethyl]guanidine
  (2) N-cyano-N'-methyl-N''-[2-((3-methoxy-4-methylamino-2-pyridyl)methylthio)ethyl]guanidine

EXAMPLE 22

1-Methylsulphinyl-1-methylthio-2-nitroethylene

Hydrogen peroxide (30%, 100 volume, 113 ml) was added over 15 minutes to a stirred solution of 1,1-bis-methylthio-2-nitroethylene (165 g) in acetic acid (4,500 ml) at 60°, and the mixture was stirred at 60° for 17 hours. The mixture was evaporated to a residue which was crystallised from butanone to give the title product as a mixture of the "Z" and "E" isomers m.p. 137°-143°. Further recrystallisation gave one isomer 145°-148° and the mother liquors were evaporated to a residue which was recrystallised from dimethoxymethane to give the other isomer m.p. 90°-93°.

EXAMPLE 23

Treatment of
(a) N-cyano-N''-methyl-N''-[2-(3-methoxy-2-pyridyl-methylthio)ethyl]guanidine, (b) 1-methylamino-1-[2-((3-methoxy-2-pyridyl)-methylthio)ethylamino]-2-nitroethylene
(c) N-cyano-N'-methyl-N''-[2-(4-methoxy-2-pyridylmethylthio)ethyl]guanidine
(d) 1-methylamino-1-[2-((4-methoxy-2-pyridyl)methylthio)ethylamino]-2-nitroethylene with hydrogen chloride in ethanol gives the corresponding hydrochloride salts.

EXAMPLE 24

A solution of 2-[2-aminoethylthiomethyl]-3-methoxypyridine in ethanol is added to a stirred solution of N-benzoyl dimethyldithioimidocarbonate in ethanol and the mixture is stirred overnight at room temperature. The purified product is treated with methylamine in ethanol and the resultant benzoylguanidine is hydrolysed by refluxing with aqueous hydrochloric acid to give N-methyl-N'-[2-(3-methoxy-2-pyridylmethylthio)ethyl]guanidine.

EXAMPLE 25

A solution of N-cyano-N'-[2-((3-methoxy-2-pyridyl)methylthio)ethyl]-S-methylisothiourea in saturated ammoniacal ethanol is heated in a pressure vessel at 95° for 16 hours and the mixture purified by chromatography and recrystallisation to give N-cyano-N'-[2-((3-methoxy-2-pyridyl)methylthio)ethyl]-guanidine.

EXAMPLE 26

Heating
(a) N-cyano-N'-[2-((3-methoxy-2-pyridyl)methylthio)-ethyl]-S-methylisothiourea
(b) 1-methylthio-1-[2-((3-methoxy-2-pyridyl)methylthio)ethylamino]-2-nitroethylene with 2-aminoethanol in ethanol results in the production of (a) N-cyano-N'-(2-hydroxyethyl)-N''-[2-((3-methoxy-2-pyridyl)methylthio)ethyl]guanidine
(b) 1-(2-hydroxyethylamino)-1-[2-((3-methoxy-2-pyridyl)methylthio)ethylamino]-2-nitroethylene.

EXAMPLE 27

Pharmaceutical composition:

| | |
|---|---|
| N-cyano-N'methyl-N''-[2-(3-methoxy-2-pyridyl-methylthio)ethyl]guanidine | 150 mg |
| Sucrose | 75 mg |
| Starch | 25 mg |
| Talc | 5 mg |
| Stearic Acid | 2 mg |

The ingredients are screened, mixed and filled into a hard gelatin capsule.

EXAMPLE 28

Pharmaceutical composition:

| | |
|---|---|
| N-cyano-N'-methyl-N''-[2-(3-methoxy-2-pyridyl-methylthio)ethyl]guanidine | 200 mg |
| Lactose | 100 mg |

The ingredients are screened, mixed and filled into a hard gelatin capsule.

What is claimed is:

1. A compound of the formula:

$$\text{Het}-CH_2Z(CH_2)_n NHC \underset{NHY}{\overset{X}{\diagup}}$$

wherein Het is a grouping of the formula:

wherein R' is lower alkyl or $-(CH_2)_pA$ where p is 2 to 4 and A is hydroxy, lower alkoxy or dimethylamino; $R^2$ is hydrogen, lower alkyl, lower alkoxy, amino, halogen or methylamino; or $-OR'$ and $R^2$ can together form a $-O(CH_2)_qO-$ group attached to adjacent carbon atoms on the pyridine ring, where q is 1 to 4; Z is sulphur or methylene; n is 2 or 3; X is $CHNO_2$; Y is hydrogen, lower alkyl or 2-hydroxyethyl; or a pharmaceutically acceptable acid addition salt thereof.

2. A compound of claim 1 wherein the 6-position of the pyridine ring is unsubstituted.
3. A compound of claim 1 wherein $-OR'$ and $R^2$ are in the 3 and 4 position of the pyridine ring comprising Het.
4. A compound of claim 1 wherein $R^2$ is hydrogen.
5. A compound of claim 4 wherein $-OR'$ is in the 3 position of the pyridine ring comprising Het.
6. A compound of claim 1 wherein R' is lower alkyl.
7. A compound of claim 6 wherein R' is methyl.
8. A compound of claim 1 wherein Z is sulphur.
9. A compound of claim 1 wherein n is 2.
10. A compound of claim 1 wherein Y is lower alkyl.
11. A compound of claim 1 wherein Y is methyl.
12. A compound of claim 1, said compound being 1-methylamino-1-[2-(3-methoxy-2-pyridylmethylthio)ethylamino]-2-nitroethylene.
13. A compound of claim 1, said compound being 1-methylamino-1-[2-(3-ethoxy-2-pyridylmethylthio)ethylamino]-2-nitroethylene.
14. A compound of claim 1, said compound being 1-methylamino-1-[2-(4-methoxy-2-pyridylmethylthio)ethylamino]-2-nitroethylene.
15. A pharmaceutical composition to block histamine $H_2$-receptors comprising in an effective amount to block said receptors a compound of claim 1 in combination with a pharmaceutically acceptable diluent or carrier.
16. A method of blocking histamine $H_2$-receptors which comprises administering orally or parenterally to an animal in need of blocking of said receptors in an effective amount to block said receptors a compound of claim 1.

* * * * *